United States Patent [19]

Robinson et al.

[11] 4,381,567

[45] May 3, 1983

[54] HYDRAULICALLY ACTUATED TOTAL CARDIAC PROSTHESIS WITH REVERSIBLE PUMP AND THREE-WAY VENTRICULAR VALVING

[75] Inventors: Thomas C. Robinson; Sotiris Kitrilakis, both of Berkeley, Calif.

[73] Assignee: Foxcroft Associates, San Antonio, Tex.

[21] Appl. No.: 302,596

[22] Filed: Sep. 15, 1981

[51] Int. Cl.³ .......................... A61F 1/24; A61M 1/03
[52] U.S. Cl. ..................................... 3/1.7; 128/1 D;
  417/383; 417/394; 417/395
[58] Field of Search ............. 3/1.7; 128/1 D, DIG. 3;
  417/383, 388–390, 394, 395

[56] References Cited

U.S. PATENT DOCUMENTS

| | | | |
|---|---|---|---|
| 3,182,335 | 5/1965 | Bolie | 3/1.7 |
| 3,208,448 | 9/1965 | Woodward | 3/1.7 X |
| 3,273,594 | 9/1966 | Mayer | 3/1.7 X |
| 3,327,322 | 6/1967 | Norton | 3/1.7 |
| 3,337,878 | 8/1967 | Bolie | 3/1.7 |
| 3,434,162 | 3/1969 | Wolfe | 3/1.7 |
| 3,449,767 | 6/1969 | Bolie | 3/1.7 |
| 3,452,738 | 7/1969 | Jones | 128/1 D |
| 3,452,739 | 7/1969 | Guarino | 128/1 D |
| 3,456,444 | 7/1969 | Rishton | 128/1 D X |
| 3,457,909 | 7/1969 | Laird | 128/1 D X |
| 3,465,746 | 9/1969 | Guarino | 128/1 D |
| 3,478,695 | 11/1969 | Goranson et al. | 3/1.7 X |
| 3,484,616 | 12/1969 | Baumgardner et al. | |
| 3,487,784 | 1/1970 | Rafferty et al. | 128/1 D X |
| 3,518,702 | 7/1970 | La Russa | 3/1.7 |
| 3,536,423 | 10/1970 | Robinson | 3/1.7 X |
| 3,541,612 | 11/1970 | Carney | 3/1.7 |
| 3,550,162 | 12/1970 | Huffman et al. | 3/1.7 |
| 3,568,214 | 3/1971 | Goldschmied | 3/1.7 |
| 3,597,766 | 8/1971 | Buck | 3/1.7 |
| 3,599,244 | 8/1971 | Wortman | 3/1.7 |
| 3,641,591 | 2/1972 | Kolff | 3/1.7 |
| 3,718,044 | 2/1973 | Joyce, Jr. et al. | 3/1.7 X |
| 3,720,199 | 3/1973 | Rishton et al. | 128/1 D |
| 3,755,825 | 9/1973 | DeBakey et al. | 3/1.7 |
| 3,771,173 | 11/1973 | Lamb, Jr. | 3/1.7 |
| 3,771,174 | 11/1973 | Wortman | 3/1.7 |
| 3,783,453 | 1/1974 | Bolie | 3/1.7 |
| 3,791,769 | 2/1974 | Kovacs | 3/1.7 X |
| 3,911,898 | 10/1975 | Leachman, Jr. | 3/1.7 X |
| 3,916,449 | 11/1975 | Davis | 3/1.7 |
| 3,919,722 | 11/1975 | Harmison | 3/1.7 |
| 3,955,557 | 5/1976 | Takagi | 3/1.7 X |
| 3,974,854 | 8/1976 | Kurpanek | 3/1.7 X |
| 4,004,299 | 1/1977 | Runge | 3/1.7 |
| 4,058,857 | 11/1977 | Runge et al. | 3/1.7 |
| 4,143,661 | 3/1979 | LaForge et al. | 3/1.7 X |
| 4,173,796 | 11/1979 | Jarvik | 3/1.7 |
| 4,222,127 | 9/1980 | Donachy et al. | 3/1.7 |

OTHER PUBLICATIONS

Schuder, J. C., Stephenson, H. E., Jr., and Townsend, J. F., "Energy Transport into a Closed Chest by Means of Stationary Magnets and a Portable High-Power Oscillator," ASAIO, vol. VII, 1961, pp. 327–331.

Kwan-Gett, C., Zwart, H. H. J., Kralios, A. C., Kessler, T., Backman, K., and Kolff, W. C., "A Prosthetic Heart with Hemispherical Ventricles Designed for Low Hemolytic Action", pp. 409–415, Trans. ASAIO, vol. XVI, 1970.

Akutsu, T., and Kolff, W. J., "Permanent Substitute for Valves and Hearts,", Trans. ASAIO, vol. 4, pp. 230–235, 1958.

Burns, W. H., Loubier, R., and Bergstedt, R., "Development of an Electrohydraulic Implantable Artificial Heart," Trans. ASAIO, vol. XI, pp. 265–268, 1965.

Kolff, W. M., "An Artificial Heart Inside the Body," Scientific American, vol. 213, No. 5, Nov. 1965.

Burns, W. H., Loubier, R. J., and Farlow, J. M., "The Development of an Intrapericardial Cardiac Replacement Phase II," Trans. ASAIO, vol. XII, pp. 272–274, 1966.

Rogers, A., Williams, K. R., Morris, L. B., "Hydraulic Control of an Artificial Heart," Surgical Forum, vol. 17, pp. 159–161, 1966.

Burns, W. H., Shumacher, H. B., Jr., and Loubier, R. J., "The Totally Implantable Mechanical Heart, An Appraisal of Feasibility," Annals of Surgery, pp. 445–456, Sep. 1966.

Griffith, N. and Burns, W. H., "Development of an Electro-Hydraulic Energy Source to Power and Control Circulatory Assist Devices," Artificial Heart

*Progress Conference*, pp. 953-968, NIH, Washington, 1969.

Burns, W. H., Schumacher, H. B., Jr. and Griffith, N. J., "The Total Mechanical Cardiac Substitute", *Progress in Cardiovascular Diseases*, vol. XII, pp. 302-311, Nov. 1969.

Schuder, J. C., Gold, J., and Stephenson, H. E., Jr., "Ultra High Power Electromagnetic Energy Transport Into the Body," *Trans. ASAIO*, vol. XVII, pp. 406-410, 1971.

Burns, W. and Griffith, N., "Energy Systems for Implantable Circulatory Assist Devices," Oct. 1971, NTIS No. PB-212-928.

Kwan-Gett, C. S., von Kampen, K. R., Kawai, J., Eastwood, N., Kolff, W. J., "Results of Total Artificial Heart Implantation in Calves," *The Journal of Thoracic and Cardiovascular Surgery*, vol. 62, No. 6, pp. 880-889, Dec. 1971.

Landis, D. L., Pierce, W. S., Rosenberg, G., Donachy, J. H., and Brighton, J. A., "Long-Term In Vivo Automatic Electronic Control of the Artificial Heart," *Trans. ASAIO*, vol. XXIII, pp. 519-525, 1977.

Poirier, V., Gernes, D., and Szycher, M., "Advances in Electrical Assist Devices", *Trans. ASAIO*, vol. XXIII, pp. 72-78, 1977.

Jarvik, R. K., Olsen, D. B., Kessler, T. R., Lawson, J., English, J. and Kolff, W. J., "Criteria for Human Total Artificial Heart Implantation Based on Steady State Animal Data," *Trans. ASAIO*, vol. XXIII, pp. 535-542, 1977.

Miller, J. A., "Artificial Organs and Beyond," *Science News*, pp. 154-156, 1977.

Szycher, M., Poirier, V., and Keiser, J., "Selection of Materials for Ventricular Assist Pump Development and Fabrication," *Trans. ASAIO*, vol. XXIII, pp. 116-124, 1977.

Tsushima, N., Kasai, S., Koshino, I., Jacobs, G., Morinaga, N., Washizu, T., Kiraly, R., and Nose, Y., "145 Days Survival of Calf with Total Artificial Heart (TAH)," *Trans. ASAIO*, vol. XXIII, pp. 526-534, 1977.

Jarvik, R. K. Nielsen, S. D., Orth, J., Summers, R. L., Isaacson, M. S., and Kolff, W. J., "Development of a Reversing Electrohydraulic Energy Converter for Left Ventricular Assist Devices", NTIS PB-290-979, 1978.

Butler, K. C., Hoffman, L. C., Moise, J. C., and Thomas, D., "Development of an Electrohydraulic Energy Converter for Left Ventricular Assist Devices," NTIS PB-300-539, 1979.

*Primary Examiner*—Ronald L. Frinks
*Attorney, Agent, or Firm*—Schuyler, Banner, Birch, McKie & Beckett

[57] ABSTRACT

A total cardiac prosthesis having a pair of hydraulically actuated compressible blood pumps. An actuation chamber adjacent each blood pump receives hydraulic actuation fluid from a separate actuator pump to compress the blood pump during systole and eject blood therefrom. During diastole the actuation fluid is permitted to drain from the actuation chamber into a reservoir. One of the actuator pumps delivers actuation fluid to its associated actuation chamber through a three-way ventricular dump valve, which directs fluid directly to the reservoir during diastole. The other actuator pump is a reversible pump which repeatedly reverses its pumping direction to effect systole and diastole in its associated blood pump.

18 Claims, 11 Drawing Figures

HYDRAULICALLY ACTUATED TOTAL CARDIAC PROSTHESIS WITH REVERSIBLE PUMP AND THREE-WAY VENTRICULAR VALVING

BACKGROUND OF THE INVENTION

This invention relates to the field of cardiac prosthetic devices, and, more particularly, to hydraulically actuated total replacement artificial hearts and circulatory assist devices, including left ventricular assist devices, especially for use by and implantation in humans.

It has been estimated that between 16,000 and 50,000 patients annually are suitable candidates for implantation of a total cardiac prosthesis (TCP). Such candidates typically are disabled due to insufficient left and right ventricular function but are otherwise in good health. Many thousands more annually with inadequate left ventricular function and satisfactory right ventricular function may be candidates for a permanently implanted left ventricular assist device (LVAD).

The ideal total cardiac prosthesis must provide complete rehabilitation for the patient. Such a TCP recipient must be able to engage in gainful employment and all normal activities including moderate exercise. He should retain a substantially normal appearance and normal or near normal mobility with no significant limitations of any kind. Cardiac output effected by the TCP must be normal, adequate and sufficiently responsive to the patient's requirements to accommodate expected, sudden changes in physical activity or emotional stress level. The presence and operation of the TCP must be sufficiently unobtrusive so that the patient can largely forget that he is dependent on an artificial heart. All blood pumping functions of the TCP should be completely automatic, so that the patient performs no control or monitoring functions except for maintaining adequate power to the TCP, and responding to warnings that indicate a lack of power or serious problems requiring immediate technical or medical attention.

The intrathoracic blood pumping components of the TCP must be similar in size and weight to the natural heart. TCP life must be sufficiently long and reliability sufficiently high that risk to the patient of sudden prosthesis failure and its attendant anxiety are minimized. The formation of pannus and adherent thrombus must be prevented to avoid a compromise of blood pump function. Thrombo-emboli and excessive blood damage also must be prevented. The TCP must not damage adjacent tissues or impair organ function by toxicity and adverse tissue reactions, by mechanical trauma or compression, or by excessive local temperatures. The system must avoid skin penetrations of any kind to prevent infections that can arise from percutaneous leads. This eliminates a major risk to the patient, reduces the need for clinical observation and treatment, and reduces the maintenance of the TCP required of the patient. This ideal system must be low in cost to purchase, implant, and maintain. The frequency and extent of routine monitoring and maintenance, both medical and technical, must be low.

Serious research toward the realization of a total cardiac prosthesis has been under way since about 1957, sponsored largely by the U.S. National Institutes of Health (NIH). Researchers have directed this activity to six principal areas: (1) blood-compatible materials for the blood pumping means; (2) heart valves; (3) blood pumps; (4) blood pump actuating means; (5) power supplies and their application to the internal-blood pump actuating means; and (6) control mechanisms for the pumping function.

Many materials have been developed which apparently achieve blood compatibility. See, e.g., the recent survey and evaluation of these by M. Szycher et al in "Selection of Materials for Ventricular Assist Pump Development and Fabrication", *Trans. ASAIO*, Vol. XXIII, p. 116, 1977, incorporated herein by reference. (As used herein, *Trans. ASAIO* refers to the *Transactions American Society For Artificial Internal Organs*). While there is yet no human experience, recent materials like Biomer, Avcothane, etc., have been benign (i.e., have not caused thrombo-emboli) for periods up to 221 days in the calf. The materials for blood pumping membranes or sacs, however, must not only be benign and tissue compatible, but also able to withstand tens of pounds of force for something on the order of $10^9$ flexing cycles during a 20-year prosthesis life. Apparently, appropriate materials are nearly, if not already, realized today.

Another critical element of the blood pumping means is the valves, which permit blood flow into or out of the heart, but prevent backflow of blood. Many different types of valve prostheses have been developed and used in tens of thousands of implants to replace defective natural valves. Hence, adequate valves for a TCP appear to be well within the state of the art.

There has been a great deal of development activity in the area of blood pumps, primarily associated with LVAD's. This experience has shown that by utilizing appropriate biocompatible materials as described above, adequate and reliable blood pumps can be designed. The most common form of blood pump is comprised of an elastomeric sac or diaphragm-capped cavity. In a TCP which comprises two such blood pumps, each cavity is fitted with an inlet valve and an outlet valve. These pumping cavities replicate the function of the adjacent right and left ventricles of the natural heart.

The least developed of the aforementioned areas of activity is the development of an actuator to couple the power supply to the blood pump. In order to squeeze the blood-pumping sacs or force the diaphragm into the blood pumping cavity, pneumatic actuation means supplied from outside the body are most common. A number of mechanical actuation systems may be found in the literature. All sorts of linkages, gears, cams, etc., have been proposed, but none is known to be successful. Most of these systems are driven by an electric motor, although some have relied upon piezoelectric devices and other esoteric means. Both copulsation, the technique used by the natural heart, and alternate pulsation of left and right ventricles have been employed successfully. See Smith, L. M.; Olson, D. B., Sandquist, G., Grandall, E., Gentry, S., and Kolff, W. J., "A Totally Implantable Mechanical Heart", *Proceedings from the European Society of Artificial Organs*, Vol. 2, p. 150, 1975. Medical opinion appears to be impartial regarding this choice.

The coupling of a mechanical drive to the sensitive blood pumping diaphragm or sac is difficult to accomplish without raising excessive stresses and causing fatigue failures. Hence, the preferred coupling means is fluid, either liquid or gas. For example, one group has constructed an electric motor powdered, cam-actuated, diaphragm air pump which couples to the blood-pumping sac via pneumatic pressure. See V. Poirier et al, "Advances in Electrical Assist Devices," *Trans.*

ASAIO, Vol. XXIII, p. 72, 1977, incorporated herein by reference. The entirety of the above-described mechanism is intended to be implanted within the thoracic cavity. In the Poirier et al design the motor rotates only once per heartbeat. Because relatively large torque is required from the motor, it must use strong magnetic fields, employ high current, and is rather heavy.

Burns et al, by contrast, constructed a TCP actuation system using a 10k–40k rpm motor driving a hydraulic pump pressurizing a liquid to actuate the blood-pumping bladders. See W. H. Burns et al, "The Totally Implantable Mechanical Heart, an Appraisal of Feasibility," *Annals of Surgery*, Sept. 1966, pp. 445–456, and W. H. Burns et al, "The Total Mechanical Cardiac Substitute," *Process in Cardiovascular Diseases*, Vol. XII, No. 3, 1969, pp. 302–311, both incorporated herein by reference. However, the electromechanically actuated hydraulic switching valve used in this and similar systems to shunt hydraulic fluid back and forth between ventricular actuating chambers has a number of disadvantages. The switching valve itself is relatively large and heavy, consumes a great deal of power and is potentially unreliable. Long and large ducts required in this type of system cause undesirable large frictional and inertial losses, and long fluid acceleration times.

Another approach to hydraulic actuation taken by researchers has involved the use of a reversible pump which directly pumps fluid back and forth between the two actuating chambers. See Jarvik U.S. Pat. No. 4,173,796.

On the subject of power, up to this time most TCPs implanted in the calf have been powered pneumatically via transcutaneous tubing into the thoracic cavity. A large external console supplies the proper regimen of pressure variations in order to activate the internal blood pump. With such a system, calves have lived up to 221 days. Jarvik, "The Total Artificial Heart", *Scientific American*, Vol. 244, No. 1, pp. 74–80, January, 1981. On another tack, NIH has sponsored considerable effort on the development of internal nuclear power supplies and, to a lesser extent, of chemical fuel cells. None of this work, however, appears to be promising; in fact, the nuclear effort was terminated by the U.S. Energy Research and Development Administration. Additionally, various means of transmitting mechanical power transcutaneously have been attempted, but none appears to be promising. At present transcutaneous transmission of electricity appears to be the preferred method for powering a TCP. A second, less preferable, possibility is the supplying of electrical power through percutaneous wire penetrations, but these always pose a threat of infection and are psychologically annoying to the patient.

Several investigators have developed the technique of transcutaneous electrical power transmission. Their approach is to implant a coil under the skin. This coil functions as a transformer secondary winding, receiving power from an inductively coupled, external, mating coil juxtaposed therewith to serve as the transformer primary winding. At frequencies on the order of 17 kHz, up to 100 watts have been thus transmitted for many months across the skin of a dog, by Schuder. See, J. C. Schuder et al, "Ultra High Power Electromagnetic Energy Transport Into the Body," *Trans. ASAIO*, 1971, incorporated herein by reference. Thus, it appears that the inductive delivery across the intact skin of the approximately 30 watts needed to power a TCP is well within the state of the art.

On the subject of control of a TCP to make it sympathetic to the body, there have been many different approaches and much controversy. Some researchers have attempted to provide no active control. Others have required a control in order to achieve regular beating. See, e.g., W. H. Burns et al, "The Total Mechanical Cardiac Substitute," identified above. Some systems have attempted to control systole (i.e., the contraction phase of the cardiac cycle whose rate is one determinant of cardiac output) from the left ventricle of the TCP in order to control the systolic pressure in the aorta. Still other systems have attempted feedback control of stroke volume and beat rate.

The natural heart and at least some, if not all, TCPs are comprised of two pumps in series. The right pump receives blood from the vena cava and impels it into the pulmonary artery. The left pump receives blood from the pulmonary vein and impels blood into the main circulatory system via the aorta. These two pumps must, over time periods considerably longer than that of a few beats, pump nearly the same amount of blood. Otherwise, the delicate pulmonary circuit will either collapse or rupture from a deficiency or excess of blood pumped by the right ventricle to the left. Various investigators have included controls in their TCP systems in order to achieve the critical balance between the pumping rate of the right and left ventricles. The major intrinsic mechanism by which the natural heart controls cardiac output is described by Starling's Law, which essentially states that a ventricle will expel during systole essentially that blood which flows into the relaxed ventricle during diastole. For the right ventricle, the body controls the "tone", i.e., the pressure in the venous system, so that the pressure in the vena cava (relative to atmospheric pressure) may rise from 5 to 15 mm Hg when there is a demand for higher blood flow. This pressure change causes approximately a proportional increase in the amount of blood which flows from the vena cava through the tricuspid valve into the relaxed right ventricle during diastole.

It is important to note that the natural heart has no means to suck upon the veins. It can only produce a systolic contraction which expels blood from the ventricular chamber.

Similarly, for the left ventricle, the pressure in the pulmonary vein varies from 5 to 15 mm Hg and produces a proportional increase in blood flow into the left ventricle. If the right ventricle should temporarily pump slightly more than the left ventricle, the pressure rises in the pulmonary artery, and, as a consequence, in the pulmonary vein, causing more blood to flow into the left ventricle and thereby matching the pumping rate of the left ventricle to that of the right ventricle. Thus, the natural heart achieves the necessary balance between the two pumps in series via simple and direct fluid dynamic means. In a real sense, the heart is the servant, not the master of the circulatory system, and in particular it responds in the final analysis to the requirements of the body as reflected by the peripheral oxygen saturation. The above-described intrinsic control can maintain body function even in the absence of extrinsic humoral or neural control.

The body also neurally controls the rate at which the natural heart beats. Cardiac output is a function of the amount of blood ejected during systole, and the rate at which the heart beats. For all but the most strenuous activity, the systolic stroke volume per beat remains substantially constant. Thus, cardiac output is primarily a function of beat rate (i.e., the number of beats per minute). Heart rates can vary from a low of about 40 to as high as 220 beats per minute in a young person and ordinarily from about 60 to 150 bpm in an adult. Cardiac output of the natural heart can vary from about 4 to as high as 24 liters per minute, the latter being the case of a trained athlete. Experience with pacemakers and transplanted natural hearts shows that beat rate control via neural sensors is unnecessary for a satisfactory life. The hundreds of natural hearts which have been transplanted operate at their own beat frequency, unresponsive to the body's neural demands because there is no neural connection.

The natural control system also ensures that the systolic pressure in the aorta does not drop below about 80 mm Hg, in order to maintain adequate circulation to the brain. The mean pressure in the aorta is established by cardiac output and the peripheral resistance of the vascular systems. In some of the TCPs which previously have been developed, a control means has been provided to maintain pressure in the aorta and atrium within a reasonable range. On the other hand, there is evidence from natural heart transplants that such control is unnecessary; transplanted human hearts have no neural connections to the host body and hence their systolic rates are not related to neural control, yet people with such transplants have been able to lead meaningful lives. It may be concluded that a TCP can be satisfactorily operated without such control. The evidence above teaches that a workable TCP can be made to approximate the natural heart's Starling's Law behavior with relatively simple control operations.

Thus, a TCP is now technically feasible provided that a competent design is constructed. The critical blood pumping technology appears to be well established and adequate for long-term survival of the recipient. Benign power transmission across the skin can obviate the portent of infection of the thoracic cavity transmitted via percutaneous leads. One major area where satisfactory progress is lacking, however, is the provision of a practical blood pump actuating mechanism. What is needed is a simple, lightweight, reliable, transcutaneously supplied, electrically-driven actuator. This objective is the one to which the present invention is principally addressed.

SUMMARY OF THE INVENTION

Accordingly, it is an object of the present invention to provide a hydraulic actuation system for use in TCPs and circulatory assist devices which obviates many of the drawbacks of the prior art actuation systems.

More specifically, it is an object of this invention to provide a simple and reliable hydraulically actuated cardiac prosthesis, especially a TCP.

Another object of the invention is to provide a total cardiac prosthesis which is substantially unobtrusive and permits the patient to engage in all normal activities, without significant limitations of any kind.

Another object of the invention is to provide a total cardiac prosthesis wherein all blood pumping functions are completely automatic, and wherein minimum patient attention is required to maintain prosthesis operation.

Another object of the invention is to provide a total cardiac prosthesis which permits monitoring of mechanical and physiological information and which is provided with alarms to warn of power failures or other malfunctions.

Another object of the invention is to provide a total cardiac prosthesis which obeys Starling's Law.

These and other objects of the present invention are accomplished by providing an implantable hydraulically actuated total cardiac prosthesis comprising a pair of blood pumping chambers each having a blood inlet, a blood outlet and a flexible portion; a pair of actuation chambers each adapted to contain actuation fluid, one of the actuation chambers being operatively associated with one of the blood pumping chambers and the other actuation chamber being operatively associated with the other blood pumping chamber to cause displacement of the flexible portion of the blood pumping chambers in response to changes in volume of actuation fluid in their associated actuation chambers; an actuation fluid reservoir; actuation fluid pumping means in fluid communication with the reservoir for pumping actuation fluid therefrom; three-way valve means associated with one of the actuation chambers, the valve means being in fluid communication with its associated actuation chamber, the pumping means and the reservoir, and being adapted to alternately and repetitively direct actuation fluid from the pumping means to its associated actuation chamber and then from its associated actuation chamber to the reservoir; and reversible pump means in fluid communication with the other actuation chamber and the reservoir for alternately and repetitively directing actuation fluid from the reservoir to its associated actuation chamber, and then from its associated actuation chamber to the reservoir.

BRIEF DESCRIPTION OF THE DRAWINGS

The novel features of the invention are set out with particularly in the appended claims, but the invention will be understood more fully and clearly from the following detailed description of the invention as set forth in the accompanying drawings, in which:

DETAILED DESCRIPTION

The present invention is based at least in part on the discovery of a new approach to the controlled hydraulic actuation of blood pumps for use in a total cardiac prosthesis. This actuation method and the various mechanical forms suitable for practicing it are described below.

The TCP System

Figure 1:
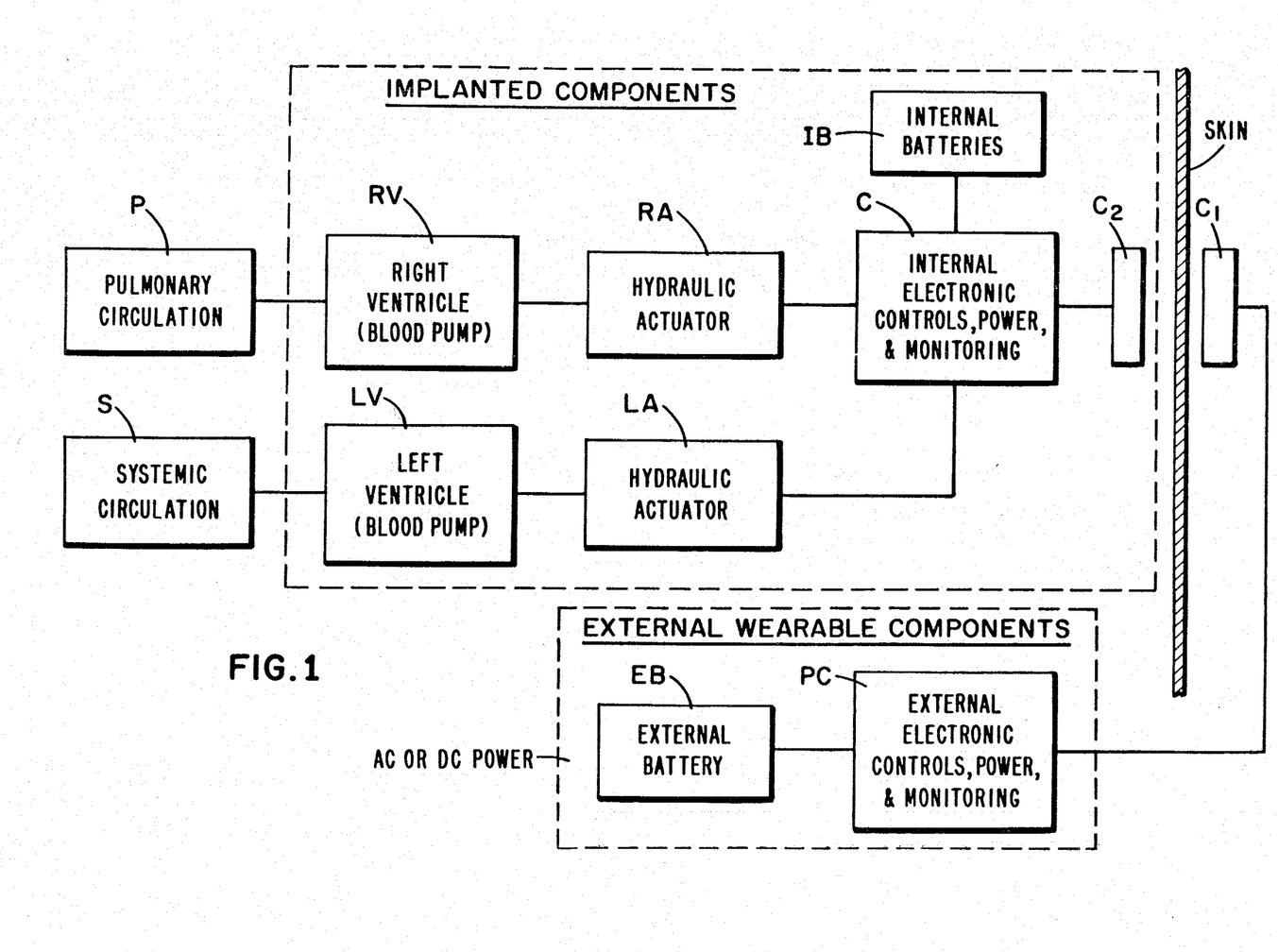
FIG. 1 is a block diagram showing the major components of a total cardiac prosthesis system according to the present invention.

FIG. 1 schematically illustrates the basic components of a TCP system according to the invention and the interaction of these components with the physiological systems of the patient. The pulmonary circulation P is maintained by a right ventricular blood pump RV. The systemic circulation S is maintained by a left ventricular blood pump LV. In the preferred embodiment of this invention each of the ventricular blood pumps is powered by a separate hydraulic actuator, RA for the right blood pump and LA for the left blood pump. The operation of the actuators RA and LA is controlled and monitored by an internal electronic control, power and monitoring circuit C which is powered at times by internal batteries IB. Most of the time, however, power is derived from an external power supply comprising an external battery EB and power circuit PC. External battery EB is rechargeable from a conventional power supply, such as household AC current or automotive DC current. Power is delivered transcutaneously to the implanted components by magnetic induction from a primary coil $C_1$ to a secondary coil $C_2$.

Preferably, the blood pumps and actuators are implanted within the thoracic cavity, while the internal electronic controls C and internal batteries IB are implanted outside of the thoracic cavity, preferably near the skin so as to permit easy replacement or servicing of these components by minor surgery. Of course, secondary coil $C_2$ must be located close to the skin for efficient inductive energy transfer.

Blood Pumps

The blood pumps of the TCP system according to this invention have essentially the same size, configuration and function as the natural heart. These functions include the same stroke volume capability, the same beat rate range, the same atrial filling pressure range and the same arterial pressure range and profile as in a healthy heart.

Blood pumps suitable for use according to the present invention can be of any of the known designs which are capable of being actuated by hydraulic actuation systems. This class includes systems in which the actuation fluid does work directly on a component of the blood pump as well as those systems in which the hydraulic fluid is coupled to the blood pump by indirect means, such as by magnetic coupling. Of primary interest, however, are those blood pump types in which the hydraulic fluid acts directly on a flexible portion of the blood pump. Examples of this type of blood pump include sac-type and membrane-capped cavity types generally known in the art. The preferred blood pumps for use in the TCP of this invention are of the membrane type (sometimes called bladder-type).

These preferred blood pumps essentially comprise a ventricular chamber containing blood inflow and outflow valves. The right and left ventricular blood pumps are generally of the same design except that the housings contain inflow and outflow ducts with orientations necessary to achieve appropriate implantability and fit.

Figures 2, 4:
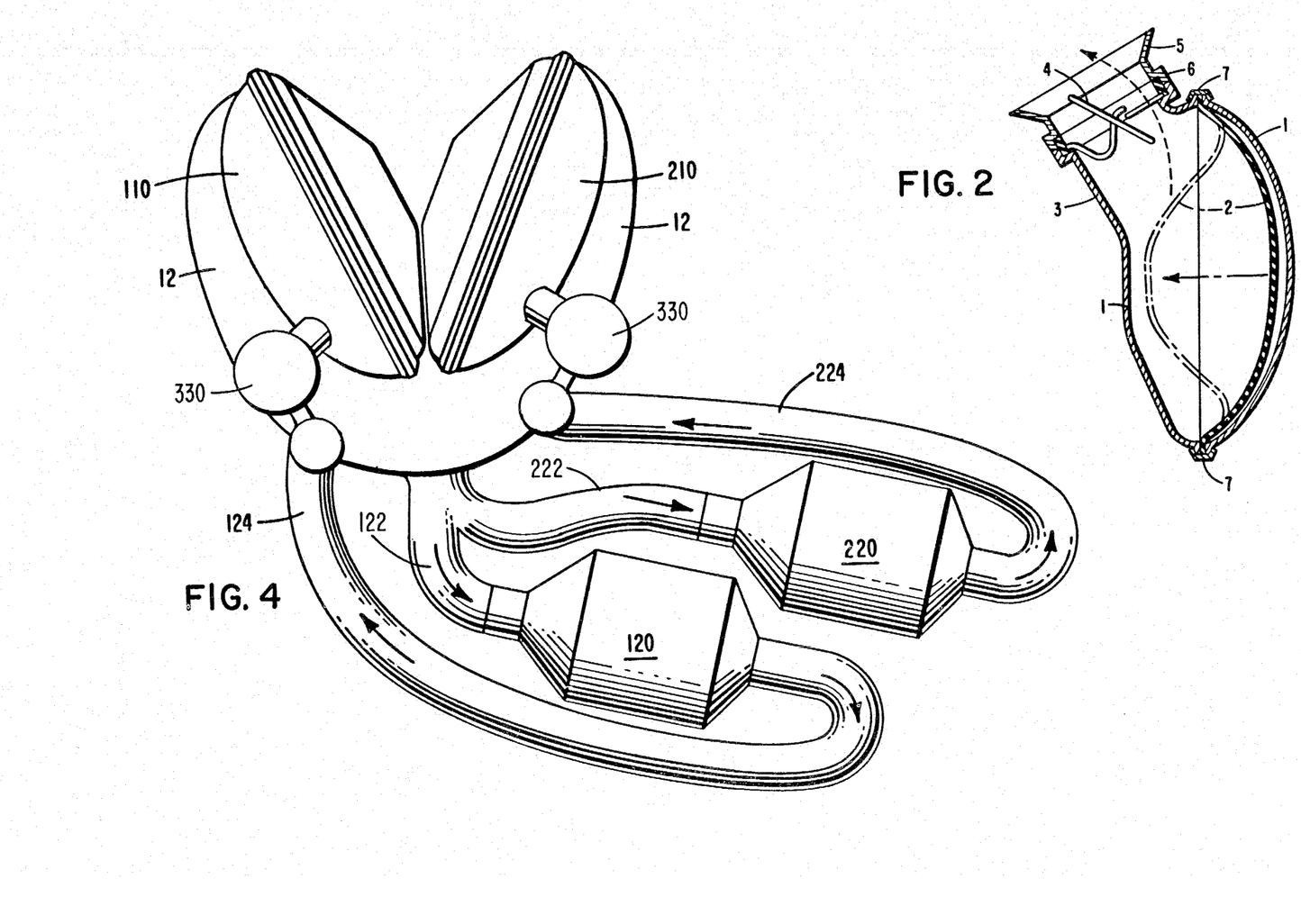
FIG. 2 is a sectional view of one type of blood pump suitable for use in a TCP according to the present invention.
FIG. 4 is a schematic illustration of the actuation fluid flow paths for the embodiment of FIG. 3.

One preferred form of blood pump is schematically illustrated in FIG. 2. The blood pump includes a two-piece rigid housing 1 in which is mounted a flexible membrane, or bladder 2, which is fabricated from an elastomeric material. The housing parts 1 and bladder 2 are secured together at their peripheries by a clamping ring 7. As the blood pump fills with blood during diastole, the flexible membrane assumes the position shown in FIG. 2 in solid lines. As hydraulic fluid is added to the housing on the non-blood side of the membrane (in a manner later described), the change in hydraulic fluid volume causes displacement of the membrane to the position shown in dotted lines. As the membrane is displaced toward the opposite housing wall, blood is forcibly expelled from the blood pump. The membrane should be of such a design that the displacement or deformation occurs uniformly and consistently with each flexing stroke. The membrane also should be designed to intrinsically avoid blood damaging contact with any portion of the rigid housing, and/or extrinsic control means should be provided to so limit the excursion of the membrane.

The blood pumping chamber is provided with a blood outflow duct 3 containing a suitable prosthetic outflow valve device 4. An inflow duct (not shown) with a suitable prosthetic inflow valve also is provided. An example of suitable mechanical prosthetic valves are Bjork-Shiley valves although numerous other designs also may be employed. The blood pump inflow and outflow tracts preferably are connected respectively to known types of atrial cuffs 5 and arterial grafts (not shown) by snap-on quick-connect fittings 6 of any suitable design which facilitate surgical implantation of the TCP. The cuffs and grafts preferably are anastomosed to the atrial remanent and the aorta or pulmonary artery before the blood pumps are connected thereto.

The blood pumping membrane 2 preferably is of the single layer type formed from a high strength elastomeric biocompatible material. Polyurethane-based polymers such as Biomer and Avcothane are among the suitable materials for this application. These types of materials have been shown to exhibit high endurance and reliability in blood pumping operations. It is also important that the membrane of the blood pump exhibit low adhesion of thrombus and low generation of thrombo-emboli. The housing is formed of a suitable rigid metallic or plastic material, such as stainless steel coated with polyurethane or other biocompatible coatings, or glass or carbon fiber reinforced plastic. Typically, all internal surfaces of the blood pumps are coated with a suitable biocompatible material.

A suitable blood pump for use in the TCP of the present invention should be capable of providing a range of cardiac outputs of from 2.8 to about 9.5 liters per minute employing full stroke volume and at a beat rate of from about 35 to 120 beats per minute.

Actuation System

In the TCP of the present invention, the above-described blood pumps are hydraulically actuated. While any incompressible fluid which is compatible with the actuator system components can be employed, the preferred actuation fluid is physiologic saline solution (0.9 g percent NaCl) which is very close in saline composition to blood plasma. The use of saline as an actuation fluid promotes osmotic equilibrium and permits maintenance of a fixed actuation fluid inventory. It also eliminates the problems associated with the use of certain other actuation fluids such as silicone oils, including diffusion of these oils into the body or diffusion and mixing of body fluids into the actuation fluid which can cause degradation of the polymer materials in the flexible membrane.

The actuation system of the present invention for one blood pump comprises four basic components: (1) an actuation fluid reservoir or compliance sac, (2) actuation fluid pumping means, (3) a ventricular actuation chamber, and (4) a three-way ventricular dump valve. The basic manner of operation of this system involves the pumping of actuation fluid from the actuation fluid reservoir into the ventricular actuation chamber to displace the flexible blood pump membrane and expel blood from the pump. The ventricular dump valve serves both to close off the actuation chamber outlet during expulsion of blood, and to drain or pump the actuation chamber fluid inventory at the end of expulsion, which permits refilling of the blood pumping chamber. The other blood pump is actuated by a reversible pump which shuttles actuation fluid back and forth between its associated actuation chamber and the reservoir.

Figure 3:
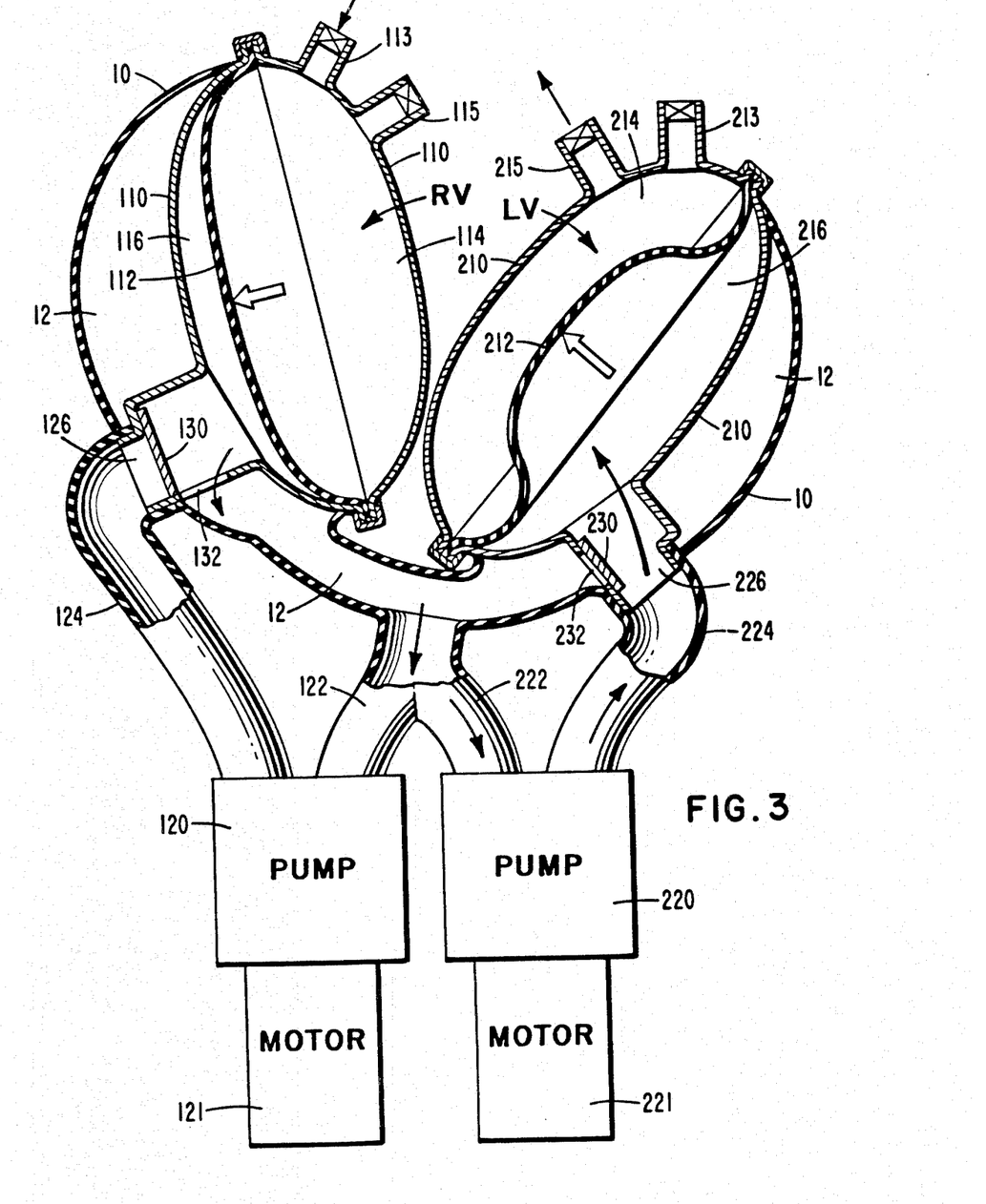
FIG. 3 is a schematic illustration of one embodiment of a total cardiac prosthesis actuation scheme according to the invention.

FIG. 3 schematically illustrates a preferred actuation system for the TCP of the invention. The blood pumps include a right ventricle RV and a left ventricle LV. Right ventricle RV is defined by a rigid housing 110 which is divided by a flexible bladder 112 into a blood pumping chamber 114 and a fluid actuation chamber 116. Similarly, left ventricle LV is defined by a rigid housing 210 which is divided by a flexible bladder 212 into a blood pumping chamber 214 and a fluid actuation chamber 216. Valved blood inlets 113, 213 and valved blood outlets 115, 215 interconnect the blood pumping chambers 114, 214 with the appropriate blood vessels.

Portions of the blood pump housings 110 and 210 are surrounded by a flexible membrane 10 which defines a fluid containing reservoir or compliance sac 12. This compliance sac faces the lung and other soft tissues in the thoracic cavity and contains actuation fluid maintained at normal intrathoracic pressure levels. During operation, the fluid is drained from each ventricle into the compliance sac during diastole and is removed from the compliance sac during systole. In the preferred form of operation, the ventricles are alternately actuated so as to minimize the change in volume of hydraulic actuation fluid in the system and therefore the overall size of the compliance sac. Copulsatile operation can, of course, be effected if desired.

In the preferred embodiment of FIG. 3, one of the blood pumps (preferably the left ventricular blood pump) is independently actuated by its own three-way valve and pumping means. The three-way valve alternately directs actuation fluid from the pumping means into the actuation chamber during systole, and then from the actuation chamber to the compliance sac during diastole. During diastole the valve blocks the flow of fluid from the pumping means. The valve can be power-operated by an electromechanical device such as a motor or solenoid, or operated by forces which vary as a function of actuation fluid flow into the actuation chamber.

As used herein, the term "three-way" applies only to valves which in one state direct fluid from one of three distinct locations to a second of the three locations, and in a second state direct fluid from the second to the third of the three locations. Such valves therefore channel fluid along only a single flow path which begins at the location of origin and terminates at the location of destination. No other flow path is provided in the valve which simultaneously carries fluid between any other locations. Of course, the single flow path referred to can comprise a plurality of channels which collectively carry the fluid from the location of origin to the location of destination. Examples of three-way valves are described below.

The pumping means preferably comprises a high speed, mixed flow, rotary pump driven by a brushless DC motor, although other suitable motor and pump designs may, of course, be used. The pump and motor bearings are totally immersed in and lubricated by the saline actuation fluid. In the preferred embodiment this hydraulic pump is designed to operate at a speed of about 7,000 to 15,000 rpm during the ventricular ejection phase (systole). During diastole the pump can continue to run at the same speed if the three-way valve is a power-operated type, or can be slowed to no less than about 1,000 to 1,200 rpm. At this low speed the pump will use less energy when pumping against the closed three-way powered valve, or will not produce sufficient fluid flow to actuate a valve of the flow-responsive type, yet will maintain a full lubricating fluid film on the bearings.

The operation of the electric motor which drives the hydraulic pumps is continuously controlled in a manner hereinafter described, preferably using back emf commutation of the type described in Chambers et al, "Development of an Electrical Energy Converter for Circulatory Devices," NTIS Publication No. PB-245 042, May, 1975, incorporated herein by reference.

The right ventricular blood pump is actuated by reversible pump means, preferably of the axial flow type. An axial flow pump is highly efficient when operating under design conditions. Such a pump has attractively low power requirements for a TCP environment when operating under the pressures encountered in connection with the pulmonary circulation system associated with the right ventricular blood pump. A high speed, mixed flow rotary pump, on the other hand, is the more attractive choice on the left ventricular side for handling the much higher pressures associated with the systemic vasculature.

Other significant advantages also obtain by using an axial flow pump. For a given flow, the inertia of the pump impeller is minimized. In contrast with most positive displacement reversible pumps, such as gear pumps, there are no contacting parts other than the bearings. In sum, reversibility, low inertia, efficiency, and smooth, balanced operation are the salient features which make an axial flow pump the preferred choice for actuating the right ventricular blood pump of the TCP of the invention.

The axial flow pump is preferably of the type which, like the mixed flow rotary pump used to actuate the left ventricle, is driven by a brushless DC motor, with the pump and motor bearings immersed in and lubricated by the saline actuation fluid. Back emf commutation is the preferred method of motor control. An example of a reversible axial flow pump suitable for use in the TCP according to the invention is illustrated and described in Jarvik, "The Total Artificial Heart," *Scientific American*, Vol. 244, No. 1, pp. 74–80, January, 1981, which is incorporated herein by reference.

Referring to FIG. 3, reversible axial flow pump 120 draws fluid from compliance sac 12 through a flexible duct 122 and delivers it to actuation chamber 116 through inlet 126 during systole. During diastole, the direction of pump 120 is reversed, forcefully draining actuation fluid from actuation chamber 116 into compliance sac 12. Alternatively, pump 120 may be shut down and permitted to "coast" during diastole, allowing the drain of actuation fluid to occur through pump 120 by virtue of the right atrial blood pressure, which forces blood into the right ventricular blood pumping chamber 114 through inlet 113. High speed, mixed flow, rotary actuating pump 220, driven by motor 221, draws fluid from compliance sac 12 through a flexible duct 222 and delivers it to actuation chamber 216 via flexible duct 224 through inlet 226. Three-way valve 230 is provided adjacent inlet 226 for controlling the inflow of actuation fluid into actuating chamber 216 from pump 220 during systole, and the outflow of actuation fluid from actuating chamber 216 into compliance sac 12 through outlet 232 during diastole.

In the operational state shown in FIG. 3, pump 220 is delivering actuation fluid to actuating chamber 216 through open inlet 226. Valve 230 has closed outlet 232, thereby preventing the escape of actuator fluid from actuating chamber 216. As pump 220 continues to operate, the volume of fluid within actuating chamber 216 increases, thereby compressing blood pumping chamber 214 and forcing blood outwardly therefrom through outlet 215 into the systemic vasculature. At the same time, pump 120 is draining actuation fluid from actuating chamber 116 into compliance sac 12. When valve 230 moves to block inlet 226 and open outlet 232, and pump 120 is driven "forwardly," the left ventricle is permitted to fill with blood, while the right ventricle is compressed to eject blood into the pumonary system through outlet 115. Of course, the valves and pumps could be operated to actuate the blood pumps in copulsatile fashion, as long as a sufficient quantity of actuation fluid is present.

FIG. 4 schematically illustrates the actuation fluid flow paths for the TCP embodiment of FIG. 3. During systole of the left ventricle, actuation fluid is delivered to the left ventricular (LV) actuation chamber by motor-driven (M) pump P from compliance sac or reservoir R through three-way ventricular dump valve V. During diastole of the left ventricle, actuation fluid drains from the left ventricular actuation chamber through valve V to reservoir R along a different flow path. During systole of the right ventricle, actuation fluid is delivered to the right ventricular (RV) actuation chamber by reversible axial pump RAP. During diastole of the right ventricle, actuation fluid is drained in reverse from the right ventricular actuation chamber to reservoir R through pump RAP, along the same flow path as that travelled during systole.

Utilization of the above-described preferred embodiment provides a number of significant advantages. Utilization of two independent actuation systems allows for independent ventricular control as well as pump and motor optimization for each ventricle to maximize efficiency. Ducting losses are minimized by mounting the dump valve on the ventricle housing. Of course, the dump valve and the reversible axial pump could be mounted remotely, connected to the ventricles by appropriate ducting. The duct which would connect the three-way valve to the left ventricle would therefore carry fluid in two directions: from the valve to the ventricle during systole, and from the ventricle to the valve during diastole. In this configuration, the blood pumping assembly, which would consist only of the right and left ventricles, would be smaller and lighter than that of the preferred embodiment, which has an integrally mounted dump valve and reversible axial pump. Hence, the intrathoracic space required for the blood pumping assembly is minimized, although some efficiency may be sacrificed due to ducting losses.

Figure 5:
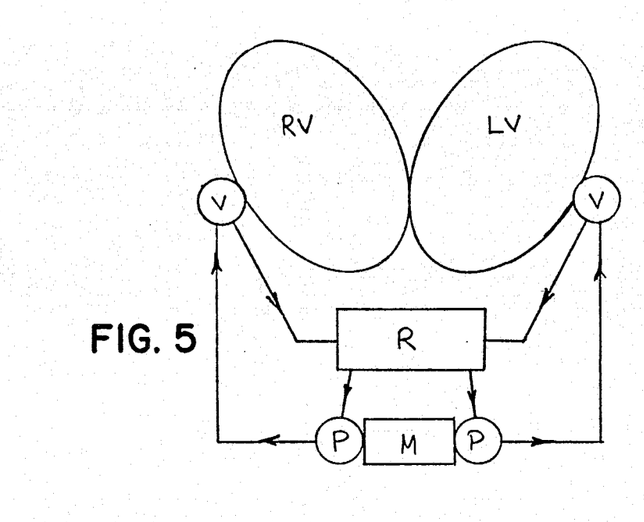
FIG. 5 is a front elevational view of a ventricular blood pump incorporating one form of three-way valve according to the invention.
Figure 6:
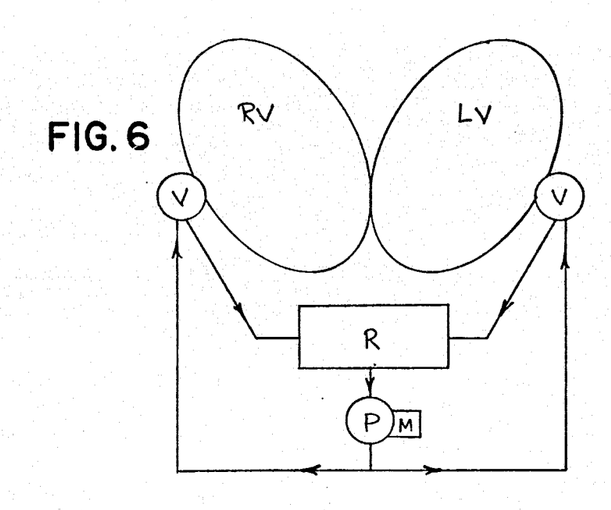
FIG. 6 is a side elevational view of the same.
Figure 7:
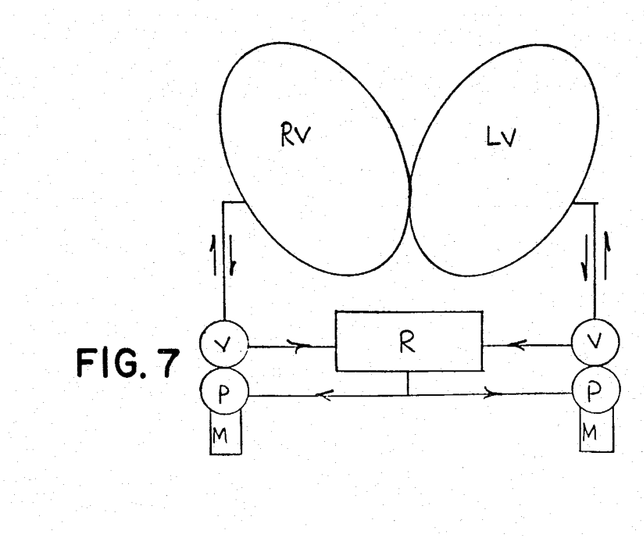
FIG. 7 is a partial sectional view thereof taken along line 7—7 of FIG. 6.
Figure 8:
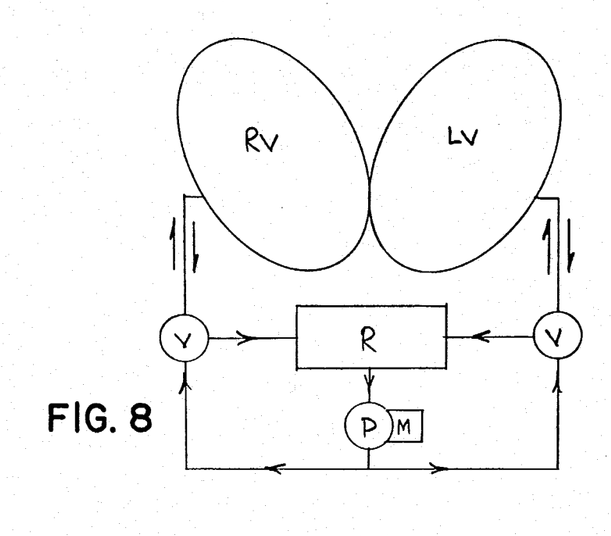
FIG. 8 is an exploded perspective view of another form of three-way valve according to the invention, showing its relationship to a ventricular blood pump.
Figure 9:
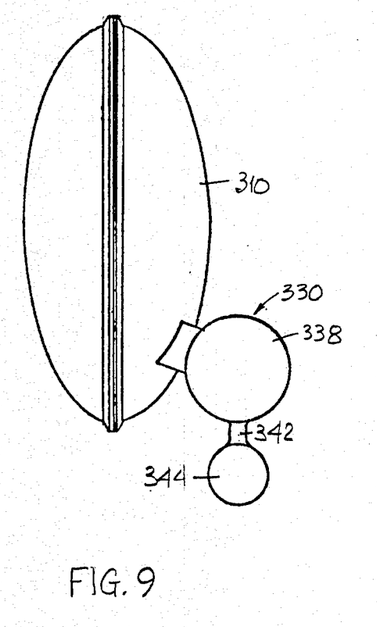
FIG. 9 is a side elevational view thereof.
Figure 10:
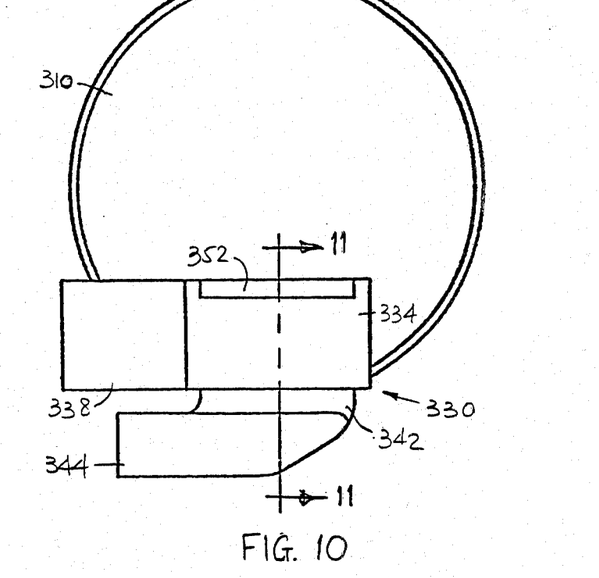
FIG. 10 is a partial sectional view thereof taken along line 10—10 of FIG. 9.
Figure 11:
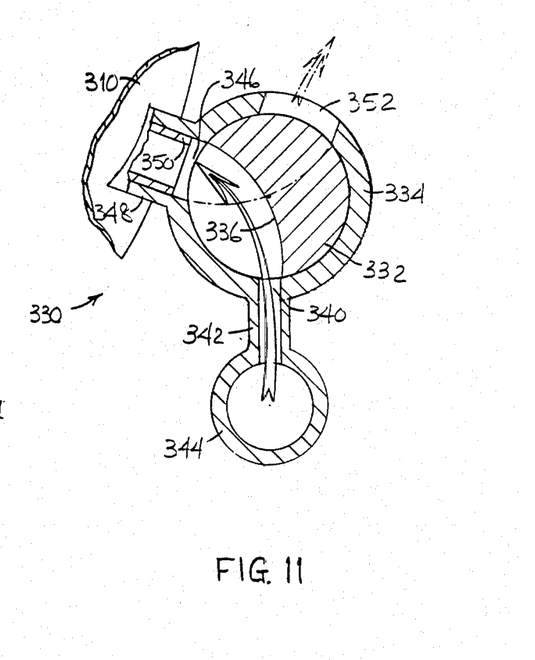
FIG. 11 is a sectional view thereof taken along line 11—11 of FIG. 9.
Figure 12:
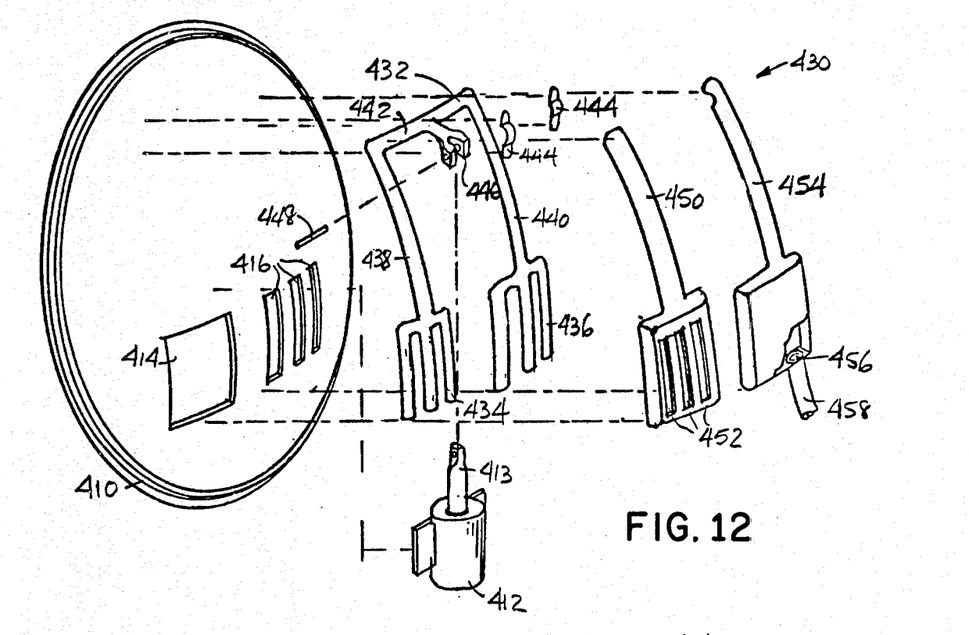
Figure 13:
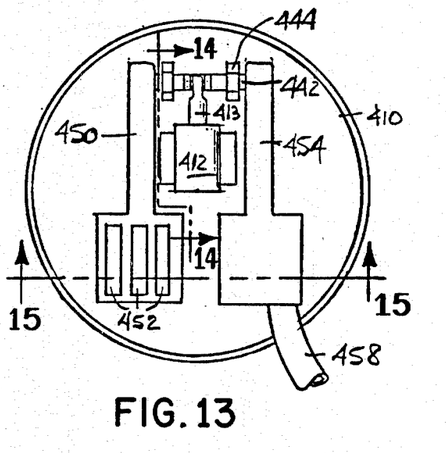
Figure 14:
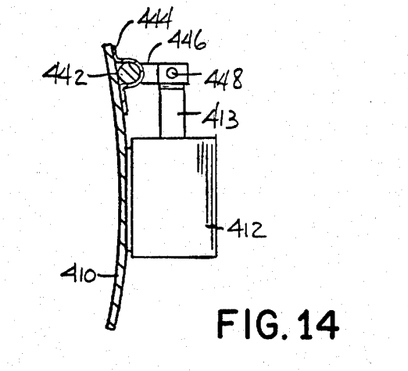
Figure 15:
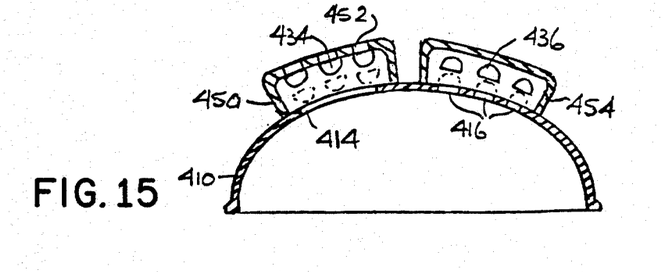
Figure 16:
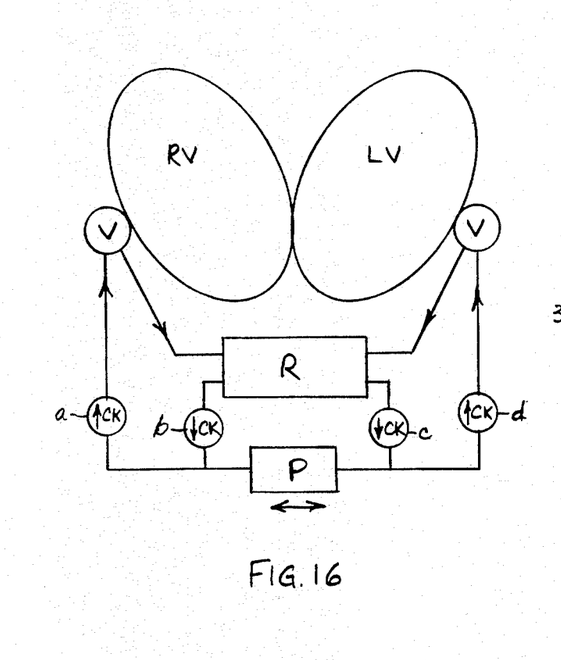

FIGS. 5, 6 and 7 illustrate one form of three-way dump valve which may be used in the cardiac prosthesis of the invention.

The three-way valve 330 is mounted directly on a ventricular blood pump 310 (preferably the left one) of the type described above. Valve 330 is a power-driven, rotary plug valve having a plug 332 which is mounted for rotation within a generally cylindrical valve body 334. Plug 332 has an arcuate groove 336 cut in its periphery so as to define, with the interior of valve body 334, a movable flow channel for directing fluid from one of three locations to another of the three locations. Rotary movement of plug 332 is effected by an electric servomotor or electromagnetic actuator 338 which is attached to the end of valve body 334 and is operatively coupled to plug 332 in a suitable known manner. Motor or actuator 338 is designed to move plug 332 to one or the other of two predetermined positions, described below, when it receives an appropriate electrical pulse from the control circuitry.

Valve body 334 includes an intake port or slit 340. An inlet manifold 342 having an inlet nipple 344 is attached to valve body 334 and communicates with inlet port 340. Nipple 344 is adapted to be connected to a duct which delivers actuation fluid to valve 330 from an actuator pump.

The interior of valve body 334 communicates with the actuation chamber within ventricle 310 through a port 346 and nipple 348. Nipple 348 also serves to secure valve 330 to ventricle 310 by engagement with ventricular nipple 350.

An outlet 352 is formed in the wall of valve body 334 through which actuation fluid is dumped from ventricle 310 into the compliance sac (not shown). During systole, with plug 332 in the position shown in solid lines in FIG. 7, actuation fluid passes through nipple 344, manifold 342 and valve body 334 into the actuation chamber within ventricle 310. During diastole, with plug 332 in the position shown in broken lines in FIG. 7, actuation fluid is free to pass from the actuation chamber within ventricle 310 through valve body 334 and out through outlet 352 into the compliance sac.

Another form of power-driven three-way ventricular dump valve is illustrated in FIGS. 8 through 11. Valve 430 is mounted on ventricle 410 and is electromagnetically actuated by a solenoid 412. The actuation chamber within ventricle 410 is provided with a large rectangular actuation fluid outlet 414 and three elongated rectangular actuation fluid inlets 416. The flow of actuation fluid through inlets 416 and outlet 414 is controlled by a finger valve assembly 432.

Finger valve assembly 432 has two sets of depending D-shaped tines or fingers 434, 436 which are respectively secured to arms 438, 440. Arms 438 and 440 are interconnected by a pivot arm 442 which is pivotally secured to ventricle 310 by brackets 444 or the like. Pivot arm 442 is provided with a lateral extension 446 which is connected to the actuating rod 413 of solenoid 412 by a pin 448. Solenoid 412 is secured to ventricle 410 beneath pivot arm 442 and between arms 438 and 440.

A housing or cover 450 overlies arm 438 and fingers 434, and is in sealing engagement with ventricle 410 and pivot arm 442. Cover 450 has three outlet slits 452 which align with fingers 434. A cover or housing 454 overlies arm 440 and fingers 436, and is sealed to ventricle 410 and around pivot arm 442. Housing 454 has a single inlet port 456 to which a duct 458 is connected for conveying actuation fluid from the actuator pump to ventricle 410. The compliance sac (not shown) surrounds at least housing 450 so that actuation fluid emerging through slits 452 is dumped directly into the compliance sac.

During systole, solenoid rod 413 is moved to an upward position in response to an appropriate electrical signal from the controller. In this mode, finger valve assembly 432 is pivoted away from ventricle 410 such that, as shown in solid lines in FIG. 11, fingers 436 uncover inlets 416 and fingers 434 cover outlet slits 452. Actuation fluid enters housing 454 and flows into the actuation chamber within ventricle 410, while closed outlet slits 452 prevent the escape of actuation fluid. During diastole, solenoid rod 413 is moved downwardly to pivot finger valve assembly 432 in the opposite direction so that fingers 434 and 436 occupy the positions shown in broken lines in FIG. 11. In this mode, inlets 416 are blocked, and outlet slits 452 are opened to permit actuation fluid to flow between fingers 434 and exit into the compliance sac.

While the above description refers to a single three-way dump valve associated with a single actuation chamber, it will, of course, be recognized that two or more dump valves of the same or different configurations can be associated with a single actuation chamber.

Control and Operation

The above-described TCP system, especially in the preferred embodiments thereof, is particularly advantageous in its ability to respond to electronic controls which are designed to cause operation of the TCP in a manner consistent with natural heart operation in humans. Basically, a modified Frank-Starling mechanism is the sole means of blood pump response to the physiological needs of the implant recipient. Each blood pump ejects whatever blood fills it, and as a result, the atrial pressure is related to cardiac output in the manner similar to the Frank-Starling response of the normal heart. Under the Frank-Starling mechanism, cardiac output is equal to venous return. Since cardiac output is equal to the heart rate times stroke volume, changes in cardiac output can be achieved either by changing the heart rate or the stroke volume. It is preferred according to the present invention to keep the stroke volume constant and achieve changes in cardiac output by changing heart rate. Constant stroke volume may be achieved by intrinsic means, e.g., by use of a stroke-limiting diaphragm, or by providing extrinsic control of diaphragm excursions in a known manner.

In the preferred embodiment of FIG. 3, heart rate control is effected by delivering controlled intermittent pulses of actuation fluid to the actuation chamber in response to a control signal supplied to the three-way ventricular pump valve, to the motor of its associated pump, and to the motor of the reversible pump by control circuit C (FIG. 1). This control signal causes the ventricular dump valve to close and open appropriate ports in the manner described above, and controls pump motor speed of the two pump motors involved. This control signal can be generated in response to any of a number of known measurable variables which provide information that can be employed to effect blood pump operation to ensure that the physiologic requirements of blood flow are met. One such variable is atrial pressure, which can be measured in a known manner using pressure transducers. Landis et al, "Long-Term in Vivo Automatic Electronics Control of the Artificial Heart", Trans. ASAIO, Vol. XXIII, pp 519-525, 1977, herein incorporated by reference.

In the preferred manner of operating the TCP of the present invention, ventricular ejections will alternate thereby conserving actuation fluid. As indicated previously, however, copulsatile operation can be effected with a concomitant increase in the hydraulic reservoir capacity. One of the significant advantages of the preferred TCP design of the present invention is that by the use of separate actuation mechanisms for each ventricle, separate and optimal control of each ventricle can be achieved.

Power Supply

In the preferred embodiment power to energize the electric motors and control electronics is furnished by electromagnetic induction across the intact skin of the patient. Telemetry signals for indicating system and patient information are also transmitted in this manner, albeit usually in the opposite direction. This type of power supply and telemetering system has been described in the prior art and consists generally of a high frequency coupling transformer which includes a small flat internal coil implanted subcutaneously and a larger flat external coil which is mounted over the implanted coil. The external coil can be carried in a vest, belt or other article of clothing. In practice, this energy transmission system can tolerate considerable movement of the external coil relative to the internal coil without adversely affecting the transfer of power or information into or out of the system. Power to drive the external coil can be provided in an external electronics pack which can contain batteries, battery charging electronics and other electronic systems useful in the monitoring of system and patient functions. Also included in the monitoring electronics are provisions for audible or visible alarms which warn of incipient malfunctions or problems.

The external battery pack can be designed to provide several hours of mobility for the patient. This battery pack when depleted can be easily replaced with a fully charged one. It can also be charged from AC line current when the patient is "plugged into the wall" or while the patient is using another battery pack, or from an automative DC battery while motoring.

An implanted internal battery pack will also provide a temporary source with complete freedom from any external power. This will permit the recipient to undertake acts such as bathing and the like and will provide sufficient time to change external power sources, i.e., changing the vest or external battery packs. In the preferred embodiment this internal battery will be located subcutaneously for easier periodic replacement.

While certain specific embodiments of the invention have been described with particularity herein, it should be recognized that various modifications thereof will appear to those skilled in the art. Therefore, the scope of the invention is to be limited solely by the scope of the claims appended hereto.

We claim:

1. An implantable hydraulically actuated total cardiac prosthesis comprising:
 a pair of blood pumping chambers each having a blood inlet, a blood outlet and a flexible portion;
 a pair of actuation chambers each adapted to contain actuation fluid, one of said actuation chambers being operatively associated with one of said blood pumping chambers and the other of said actuation chambers being operatively associated with the other of said blood pumping chambers to cause displacement of the flexible portion of said blood pumping chambers in response to changes in volume of actuation fluid in their associated actuation chambers;

an actuation fluid reservoir;

actuation fluid pumping means in fluid communication with said reservoir for pumping actuation fluid therefrom;

three-way valve means associated with one of said actuation chambers, said valve means being in fluid communication with its associated actuation chamber, said pumping means and said reservoir, and being adapted to alternately and repetitively direct actuation fluid from said pumping means to its associated actuation chamber and then from its associated actuation chamber to said reservoir; and reversible pump means in fluid communication with the other actuation chamber and said reservoir for alternately and repetitively directing actuation fluid from said reservoir to its associated actuation chamber, and then from its associated actuation chamber to said reservoir.

2. The invention of claim 1 wherein said actuation fluid reservoir comprises a compliant zone defined at least in part by a flexiblewall portion made from biocompatible elastomeric material.

3. The invention of claim 2 wherein said actuation fluid reservoir comprises a separate compliant zone associated with each of said actuation chambers, defined at least in part by a flexible wall portion made from biocompatible elastomeric material, said compliant zones communicating with each other, said pumping means, said reversible pump means, and said valve means by flexible ducting.

4. The invention of claim 1 wherein said actuation fluid pumping means comprises a pump and drive motor therefor.

5. The invention of claim 4 wherein said pump is a high speed, mixed flow rotary pump.

6. The invention of claim 4 wherein said drive motor is a brushless DC electric motor.

7. The invention of claim 6 further comprising means for commutating said brushless DC electric motor.

8. The invention of claim 7 wherein said means for commutating comprises back-emf control circuitry.

9. The invention of claim 1 wherein said blood inlet and said blood outlet are provided with prosthetic valves adapted to permit the flow of blood in only one direction.

10. The invention of claim 1 wherein said blood pumping chamber comprises a variable volume zone defined in part by a flexible membrane made from biocompatible elastomeric material and in part by a rigid blood pumping chamber housing.

11. The invention of claim 1 wherein said actuation chamber comprises a variable volume zone defined in part by said flexible portion of said blood pumping chamber and in part by a rigid actuation chamber housing.

12. The invention of claim 1 wherein said valve means comprises a three-port rotary plug valve and a drive motor therefor.

13. The invention of claim 1 wherein said valve means is mounted on said actuation chamber and communicates directly with the interior thereof.

14. The invention of claim 1 further comprising means for applying electric power to said actuation fluid pumping means and said reversible pump means and associated control electronics in a patient having an implanted cardiac prosthesis.

15. The invention of claim 14 wherein said means for supplying electric power comprises an external primary coil inductively coupled to a subcutaneous secondary coil for transmitting electrical energy across the intact skin of a patient.

16. The invention of claim 1, 5, 8, 12 or 14 wherein said reversible pump means comprises an axial flow pump and a reversible motor driving said axial flow pump.

17. The invention of claim 16 wherein said reversible pump means is mounted on said actuation chamber and communicates directly with the interior thereof.

18. The invention of claim 16 wherein said reversible pump means is associated with the right blood pumping chamber which is adapted to circulate blood through the pulmonary vascular system.

* * * * *